United States Patent
Rowlands et al.

(10) Patent No.: US 7,687,792 B2
(45) Date of Patent: Mar. 30, 2010

(54) X-RAY LIGHT VALVE BASED DIGITAL RADIOGRAPHIC IMAGING SYSTEMS

(75) Inventors: John Alan Rowlands, Toronto (CA); Christie Ann Webster, Oshawa (CA); Ivaylo Koprinarov, Toronto (CA); Peter Oakham, Ottawa (CA); Stephen Germann, Burlington (CA); James Alexander Robert Stiles, Toronto (CA)

(73) Assignee: Sunnybrook Health Sciences Centre, Toronto (CA)

( * ) Notice: Subject to any disclaimer, the term of this patent is extended or adjusted under 35 U.S.C. 154(b) by 379 days.

(21) Appl. No.: 11/704,371

(22) Filed: Feb. 9, 2007

(65) Prior Publication Data

US 2007/0201616 A1 Aug. 30, 2007

Related U.S. Application Data

(60) Provisional application No. 60/771,873, filed on Feb. 10, 2006.

(51) Int. Cl.
*H05G 1/64* (2006.01)
(52) U.S. Cl. .................. 250/580; 378/98.2
(58) Field of Classification Search ............ 250/580; 378/98.2, 4
See application file for complete search history.

(56) References Cited

U.S. PATENT DOCUMENTS

| | | | | |
|---|---|---|---|---|
| 3,699,347 A | * | 10/1972 | Buchan et al. | 250/550 |
| 3,700,902 A | * | 10/1972 | Buchan | 250/201.1 |
| 3,713,723 A | * | 1/1973 | Buchan | 365/121 |
| 3,754,144 A | * | 8/1973 | Caruso | 250/214 LA |
| 5,461,506 A | * | 10/1995 | Check et al. | 359/296 |
| 5,847,499 A | | 12/1998 | Rieppo | |
| 5,864,146 A | * | 1/1999 | Karellas | 250/581 |
| 6,052,432 A | * | 4/2000 | Rieppo et al. | 378/98.2 |
| 6,310,358 B1 | * | 10/2001 | Zur | 250/591 |
| 2004/0264626 A1 | * | 12/2004 | Besson | 378/4 |
| 2005/0167622 A1 | * | 8/2005 | Mitchell et al. | 250/585 |
| 2006/0018025 A1 | * | 1/2006 | Sharon et al. | 359/618 |

FOREIGN PATENT DOCUMENTS

CA 2228325 10/2002

* cited by examiner

*Primary Examiner*—David P Porta
*Assistant Examiner*—Djura Malevic
(74) *Attorney, Agent, or Firm*—Lynn C. Schumacher; Hill & Schumacher

(57) ABSTRACT

The present invention provides a digital x-ray radiographic imaging system. The system is based on a photoconductive detector and an electro-optic light modulator, where the photoconductive detector layer absorbs x-rays that have passed through an object to form an exposure of the object. The absorbed x-rays create a static optical image, which is stored in the electro-optic light modulator, allowing the capture of the optical image to continue over longer time. The optical image is digitized using a scanning system and an external light source. The image is then processed and stored by a computer. After the optical image is recorded, an erasing mechanism is used to reset the system before a new exposure is made.

71 Claims, 6 Drawing Sheets

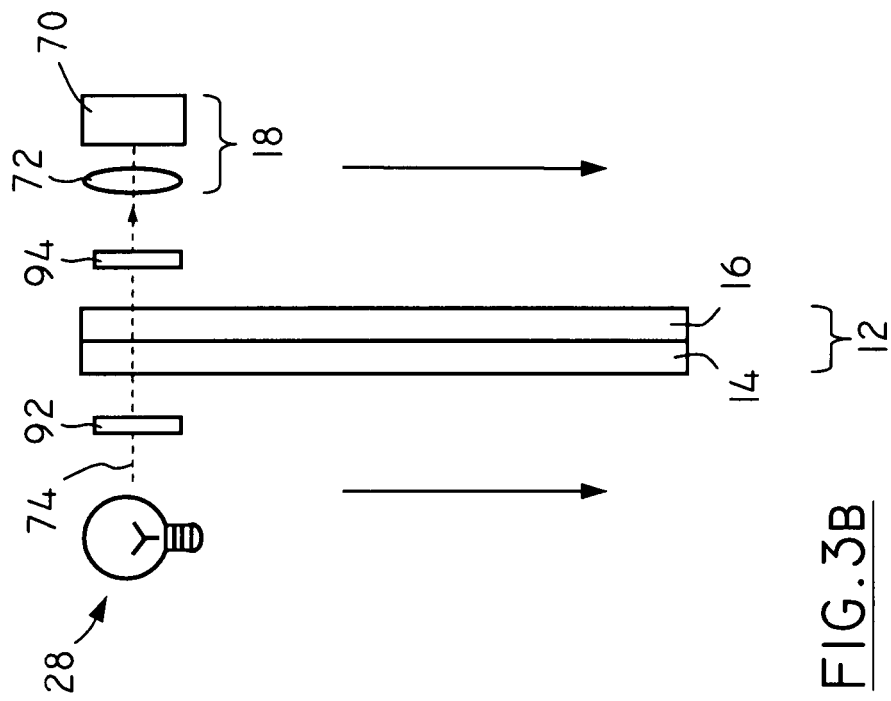
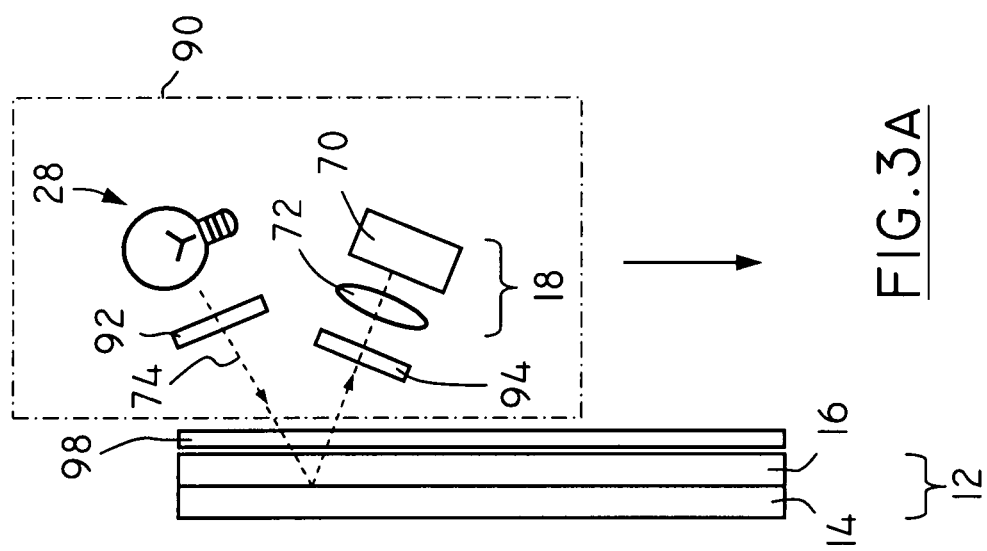
FIG. 3A
FIG. 3B

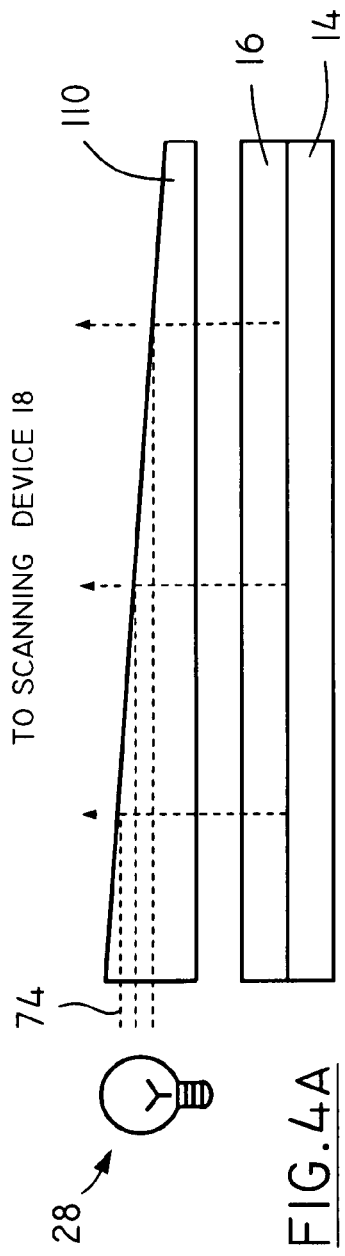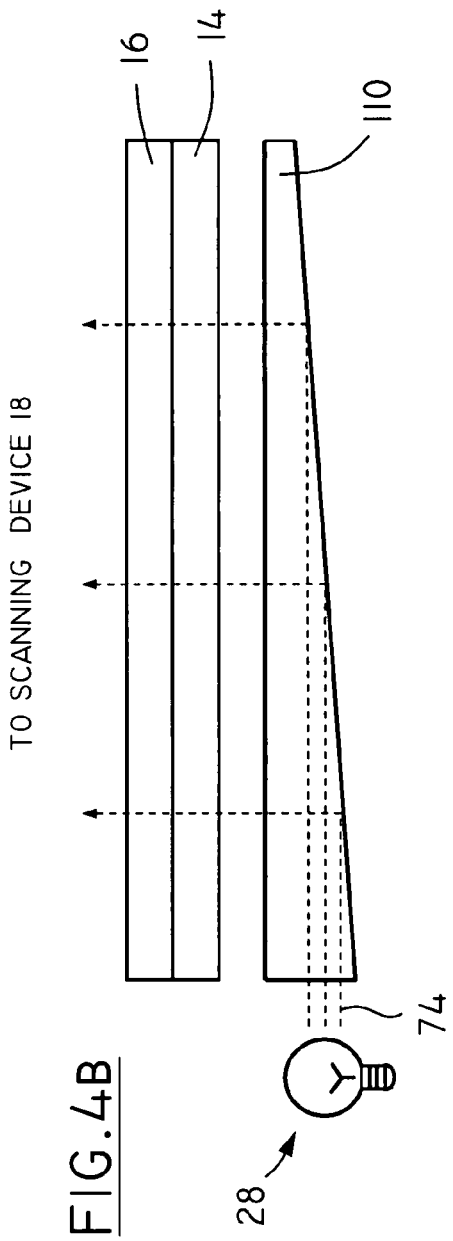

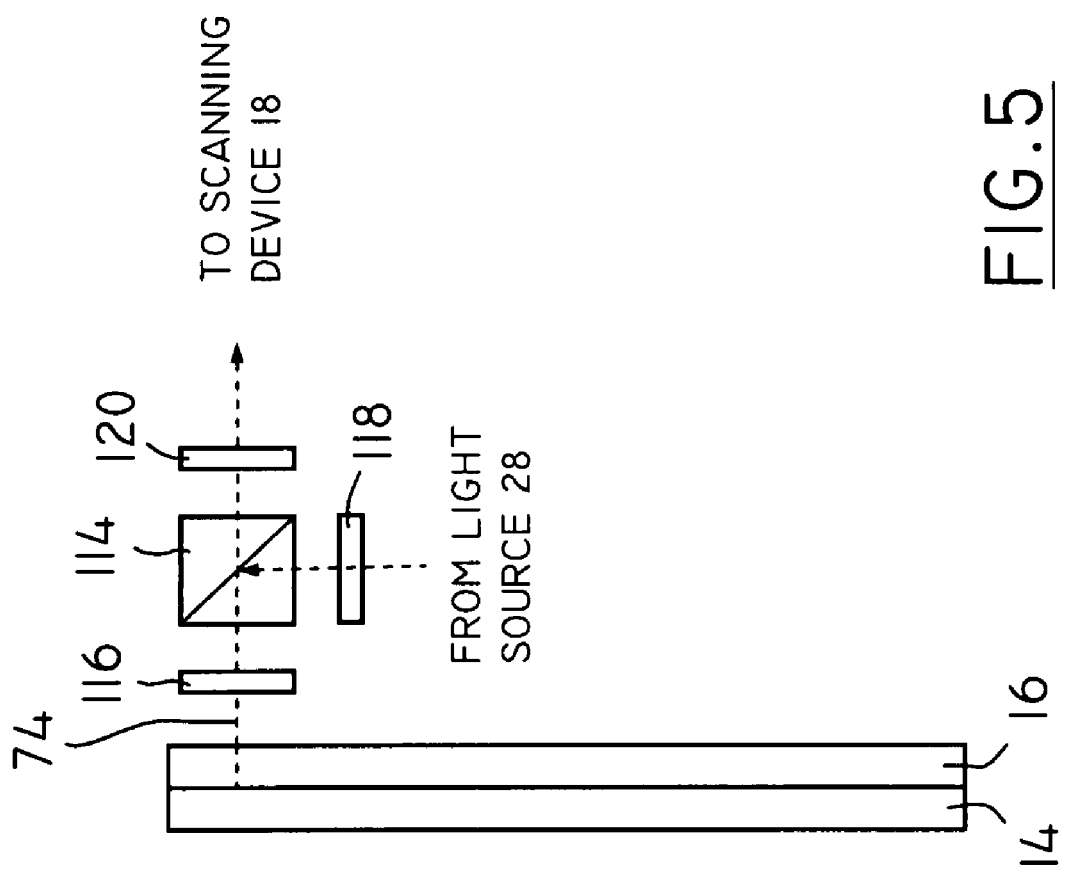

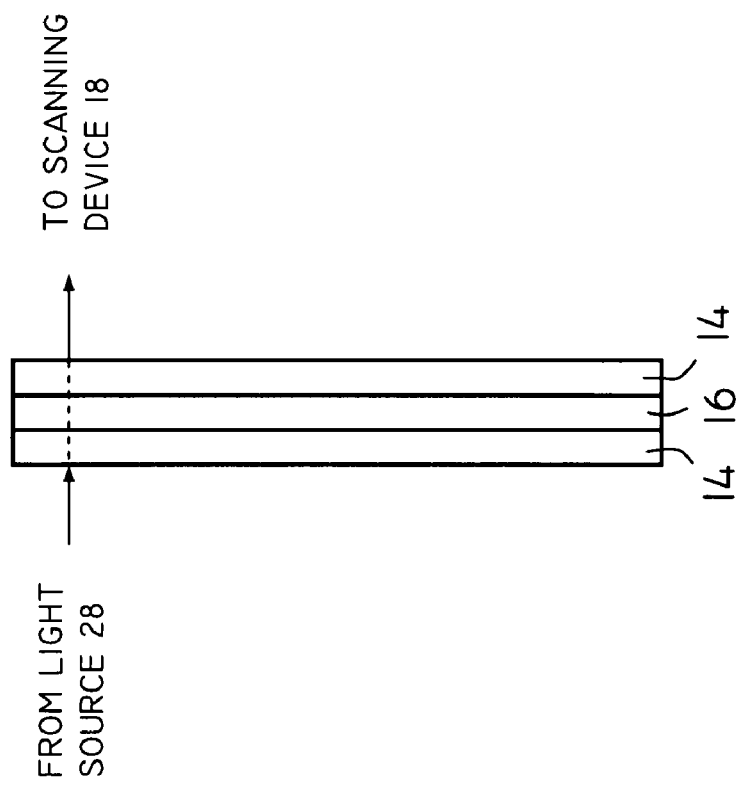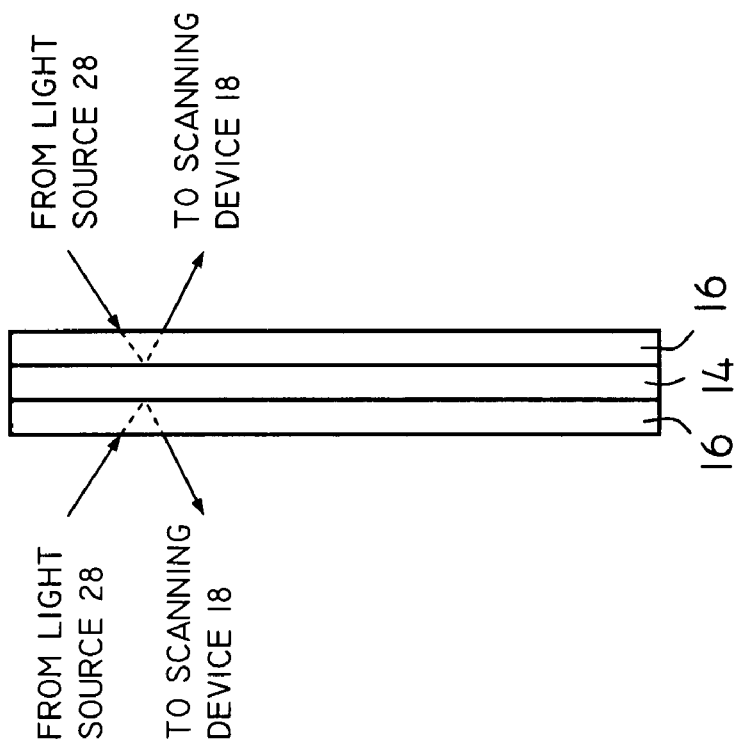

X-RAY LIGHT VALVE BASED DIGITAL RADIOGRAPHIC IMAGING SYSTEMS

CROSS REFERENCE TO RELATED U.S. PATENT APPLICATION

This patent application relates to U.S. utility patent application Ser. No. 60/771,873 filed on Feb. 10, 2006 entitled X-RAY LIGHT VALVE BASED DIGITAL RADIOGRAPHIC IMAGING SYSTEMS, filed in English, which is incorporated herein in its entirety by reference.

FIELD OF THE INVENTION

This invention relates to radiation imaging and in particular to an x-ray imaging system and a method of x-ray imaging.

BACKGROUND OF THE INVENTION

Medical x-ray imaging systems up until recently were typically based on either film or phosphor. Newer systems based on large area flat panel technology or storage phosphors enabled production of digital x-ray images. These newer systems, while providing many advantages have considerably increased initial cost compared to older film based systems.

Active Matrix Flat Panel Imagers are based on phosphor or photoconductor detectors with direct electronic readout of individual pixels. They can provide images very quickly and are therefore very useful for demanding applications, like fluoroscopy. However, Active Matrix Flat Panel Imagers are extraordinarily expensive compared to the systems they are replacing and are capable of more than is needed for some applications, like radiography. Different approaches have been considered to make a low-cost x-ray digital imaging device for general radiography.

For example, photostimulable phosphors, or storage phosphors, are currently used in Computed Radiography systems. When exposed to x-rays these phosphors capture an image, which is later released by shining a specific colour of light onto the phosphor. The readout process is separate from the exposure and makes use of a large readout device. In order to modify a Computed Radiography system for immediate readout, the reader must be made very compact with a line scanning system as opposed to current spot scanning technology, which will increase the cost of the system significantly. These systems have very poor image quality, requiring approximately four times as much radiation to achieve the same image quality as Active Matrix Flat Panel Imagers. The reason for this drop in quality is the combination of the relatively poor x-ray absorption of Computed Radiography screens and the signal losses in the reader.

Other approaches exist for digital x-ray imaging but thus far none provides the quality of Active Matrix Flat Panel Imagers at a significant cost reduction. One such method is scanned projection x-ray, where a slot reader receives a matching x-ray beam. However, generation of narrow x-ray beams is difficult and mounts significant costs. Another method is an optically demagnified x-ray screen coupled to a camera system. This system is ultimately limited by the resolution of the camera system, and the signal loss between the screen and the camera. Another approach is to directly read-out the charge on a selenium plate. However, this results in large amounts of noise.

X-ray imaging systems based on a photoconductive detector layer and an electro-optic light modulator have also been attempted. Known prior art includes the apparatus described in references 1 to 3, U.S. Pat. Nos. 6,052,432 and 5,847,499, and CA patent 2,228,325; The suggested approach thus far suffers from problems characteristic for optically-demagnified screen-camera systems. Although the image created is of high quality, and in some cases, can be acquired by the camera without significant loss of signal, the described configurations are only practical for small-area detectors. The suggested implementations do not allow the imaging system to be scaled up to the size required for radiography without sacrificing pixel density, image quality or the overall cost.

Furthermore, the decay of the image in the electro-optical light modulator present in the devices disclosed in U.S. Pat. Nos. 6,052,432 and 5,847,499, and CA patent 2,228,325 and the acquisition of multiple images to improve the image quality or the dynamic range has been proven to be impractical thus far. Work has also been done on Polymer Dispersed Liquid Crystal based systems (see references 4 and 5). Those devices also suffer from the problems described above along with rapid image degradation due to the high ionic content of Polymer-Dispersed Liquid Crystals.

It is therefore an object of the present invention to provide a novel development of a digital radiographic system based on a photoconductive detector and an electro-optic light modulator designed to store the image in the electro-optic light modulator and a method of x-ray imaging associated with it.

SUMMARY OF THE INVENTION

According to one aspect of the present invention there is provided a radiographic digital imaging system based on a photoconductive detector and an electro-optic light modulator, referred to as x-ray light valve (XLV), which absorbs x-rays that have passed through an object to form an exposure of the object. The x-rays absorbed by the photoconductor create a static optical image, which is stored in the electro-optic light modulator, allowing the capture of the optical image to continue over a prolonged time. The stored optical image is subsequently digitized by an optical scanning device.

More particularly, an embodiment of the digital radiographic imaging system comprises:

a) an x-ray light valve including a first photoconductive detector layer and an electro-optic light modulator disposed on said first photoconductive detector layer, said electro-optic light modulator being configured to store optical images induced therein for a pre-selected period of time, means for applying and removing an exposure bias potential across said x-ray light valve such that when said exposure bias potential is applied an electric field is produced in said x-ray light valve and hence across said first photoconductive detector layer, whereupon exposing said x-ray light valve to x-rays having passed through an object to be imaged to form an x-ray exposure of said object, said first photoconductive detector layer absorbing x-rays having passed through said object forming electron-hole pairs separated by said exposure bias potential thereby to form a charge image which corresponds to the absorbed x-rays creating variations in potential across said electro-optic modulator, and upon removing said exposure bias potential the charge image induces an entire static optical image of said x-ray exposure in the electro-optic light modulator, which is stored in the electro-optic light modulator and lasts for said pre-selected period of time without changes to said entire static optical image to enable capture of said entire static optical image by scanning;

b) a readout light source configured to illuminate a portion of said entire static optical image stored in said electro-optic light modulator, said variations in potential across said electro-optic modulator modulating an intensity of said readout light illuminating said portion of said entire static optical image thereby to create an optical representation of said x-ray exposure;

c) an optical imaging device positioned at a pre-selected position with respect to said x-ray light valve to receive said modulated intensity of readout light capturing said portion of said stored entire static optical image of said x-ray exposure;

d) a scanning mechanism to which said optical imaging device is attached which is configured for moving said optical imaging device with respect to said x-ray light valve to enable sequential capture of some or all portions of said entire static optical image over said pre-selected period of time; and e) a processor coupled to said optical imaging device to digitize, produce and store a digitized version of some or all portions of said entire static optical image of said x-ray exposure.

An erasing mechanism may be included to reset the XLV before a new exposure is made.

The combination of long lasting optical images with scan technology and erasing mechanisms constitutes a novel development in this field. This is in contrast to U.S. Pat. Nos. 6,052,432 and 5,847,499, and CA patent 2,228,325, which make use of the property that the image in the electro-optic light modulator starts to decay immediately after the exposure. The electro-optical light modulator in the present invention is designed to store the image on the order of minutes, allowing the camera used in the patents above to be replaced by a much less expensive scanning device.

In specific embodiments, the XLV includes an amorphous selenium detector layer and a liquid crystal cell. If desired, a potential applied across the XLV during the digitization phase can be used to bring the liquid-crystal cell to the threshold of its operating characteristic. Additionally, different voltage profiles can be applied to enhance the signal or to shift the optical response as a function of x-ray exposure.

The present invention also provides advantages in the design, making it economically attractive. For example, by replacing the camera as used U.S. Pat. Nos. 6,052,432 and 5,847,499, and CA patent 2,228,325, with a scanning device, the complexity of the imager and hence the cost of the overall system is greatly reduced. The present invention requires little external circuitry beyond a high-voltage power supply and conventional computer technology. Therefore, the manufacturing costs can be kept very low. All elements of the overall design are chosen to be easily scalable to the sizes required for medical imaging without sacrificing resolution, pixel density, or the low cost of the overall system.

According to another aspect of the present invention there is provided a method of x-ray imaging, comprising the steps of applying a potential across the photoconductor, x-ray exposure, storing the optical image in the electro-optic light modulator, digitizing by moving an optical scanning device across the optical image, erasing and resetting the XLV, processing and storing the digital data. Further methods might include calibrating the optical scanner and applying different voltage profiles across the XLV in combination with other steps.

Accordingly, the present invention also provides a method of x-ray imaging of an object, comprising the steps of:

a) applying an exposure bias potential across a x-ray light valve which includes a photoconductive detector layer and an electro-optic light modulator disposed on said photoconductive detector layer such that an electric field is produced in said x-ray light valve and hence across said photoconductive detector layer;

b) exposing said x-ray light valve to x-rays having passed through an object to be imaged to form an x-ray exposure of said object, said photoconductive detector layer absorbing x-rays having passed through said object forming electron-hole pairs separated by said exposure bias potential thereby to form a charge image which faithfully corresponds to the absorbed x-rays creating variations in potential across said electro-optic modulator;

c) removing said exposure bias potential whereupon the charge image induces an entire static optical image of said x-ray exposure in the electro-optic light modulator, said electro-optic light modulator being configured such that said electro-optic light modulator retains said entire static optical image for a pre-selected period of time without any changes to said entire static optical image to enable capture of said entire static optical image to continue over said pre-selected period of time by scanning;

d) illuminating a portion of said entire static optical image of said x-ray exposure stored in said electro-optic light modulator;

e) capturing said portion of the entire static optical image of said x-ray exposure using an optical imaging device;

f) digitizing and storing said captured portion of said entire static optical image of said x-ray exposure;

g) moving said optical imaging device with respect to said x-ray light valve using a scanning mechanism and repeating steps d), e) and f) to sequentially capture all portions of said entire static optical image within said pre-selected period of time.

A further understanding of the functional and advantageous aspects of the invention can be realized by reference to the following detailed description and drawings.

BRIEF DESCRIPTION OF THE DRAWINGS

Preferred embodiments of the invention will now be described, by way of example only, with reference to the drawings, which are not to scale, in which:

FIG. 3A is a side view of another embodiment of a scanning device, forming part of the digital radiographic imaging system of FIG. 1;

FIG. 3B is a side view of another embodiment of the scanning device, forming part of the digital radiographic imaging system of FIG. 1;

FIG. 4A is top view of another embodiment of the scanning device of the digital radiographic imaging system in accordance with the present invention;

FIG. 4B is top view of another embodiment of the scanning device of the digital radiographic imaging system in accordance with the present invention;

FIG. 5 is a side view of another embodiment of the scanning device of the radiographic imaging system in accordance with the present invention;

FIG. 6A is a side view of another embodiment of an x-ray light valve, forming part of the digital radiographic imaging system of FIG. 1; and FIG. 6B is a side view of another embodiment of an x-ray light valve forming part of the digital radiographic imaging system of FIG. 1.

DETAILED DESCRIPTION OF THE INVENTION

The systems described herein are directed, in general, to embodiments of digital radiographic imaging system. Although embodiments of the present invention are disclosed herein, the disclosed embodiments are merely exemplary and it should be understood that the invention relates to many alternative forms, including different shapes and sizes. Furthermore, the Figures are not drawn to scale and some features may be exaggerated or minimized to show details of particular features while related elements may have been eliminated to prevent obscuring novel aspects. Therefore, specific structural and functional details disclosed herein are not to be interpreted as limiting but merely as a basis for the claims and as a representative basis for enabling someone skilled in the art to employ the present invention in a variety of manner. For purposes of instruction and not limitation, the illustrated embodiments are all directed to embodiments of digital radiographic imaging systems.

As used herein, the term "about", when used in conjunction with ranges of dimensions of particles or other physical properties or characteristics, is meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present invention.

As used herein, the phrase "high-resistivity liquid crystal" refers to liquid-crystal mixtures which provide high resistivity and voltage holding ratio characteristics. However, the capability of keeping charges is considered as a system parameter, including also other parts of the liquid-crystal cell, and is not limited to the liquid crystals alone.

Figure 1:
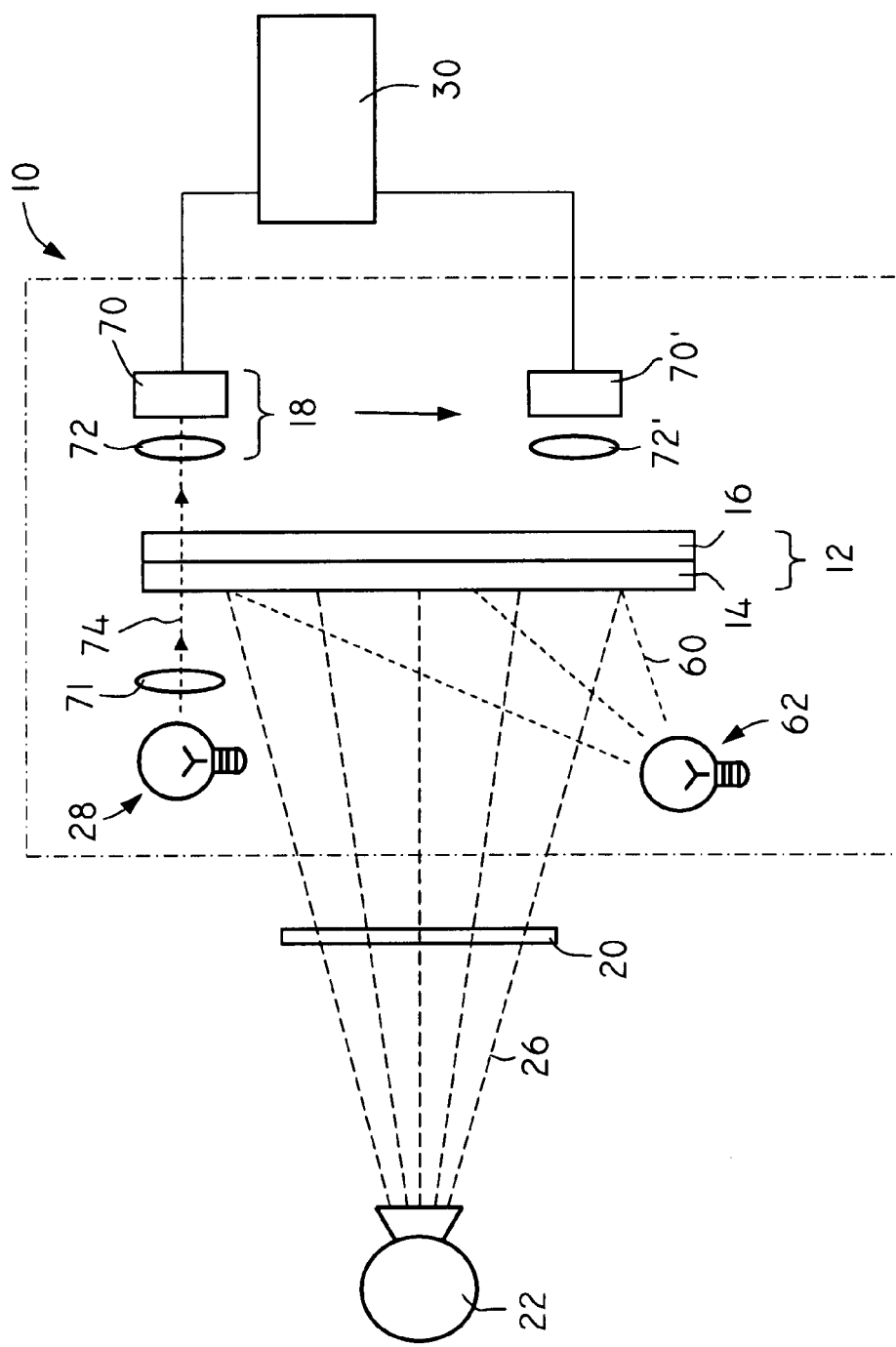
FIG. 1 shows a structure of digital radiographic imaging system produced in accordance with the present invention.

Referring to FIG. 1, digital radiographic imaging system in accordance with the present invention is shown generally at 10. The radiographic imaging system 10 allows x-rays that have passed through an object such as a patient to be captured and fed into a computer in a digital format.

The digital radiographic imaging system 10 combines an X-Ray Light Valve (XLV) 12, including a photoconductive detector layer 14 and an electro-optic light modulator 16, with a readout light source 28 and a digitizing optical scanning device 18. The XLV 12 is dimensioned so that the entire object or the desired area of interest of the object 20 can be imaged. The object 20 to be imaged is placed between the x-ray source 22 and the x-ray imaging system 10. The photoconductor layer 14 absorbs the x-rays 26 to create a static optical image in the electro-optic light modulator 16. By carefully designing or configuring the properties of the electro-optic light modulator 16 used, the image can remain stable on the order of minutes. The optical image stored in the electro-optic light modulator 16 is then digitized by using the readout light source 28 and the optical scanning device 18 and processed through a processor 30. This differs from previous technology, particularly U.S. Pat. Nos. 6,052,432 and 5,847,499, and CA patent 2,228,325, where the electro-optic light modulator is selected to allow the image to decay immediately after the exposure. The scanning approach as used in the present invention requires that the electro-optic light modulator 16 is configured or designed such that the optical image lasts for a pre-selected period of time without any decay, usually on the order of minutes.

The system 10 may include focusing optics 71 for directing and focusing light from the readout light source 28 to the x-ray light valve 12.

Although the x-ray source 22 is shown on the photoconductor 14 side of the XLV 12 in FIG. 1, its position is not limited to the indicated side. The x-ray source 22 might be arranged on either side of the XLV 12 in different implementations since the x-rays 26 will not be attenuated by the electro-optic light modulator 16 on their way to reach the photoconductor layer 14.

Figure 2:
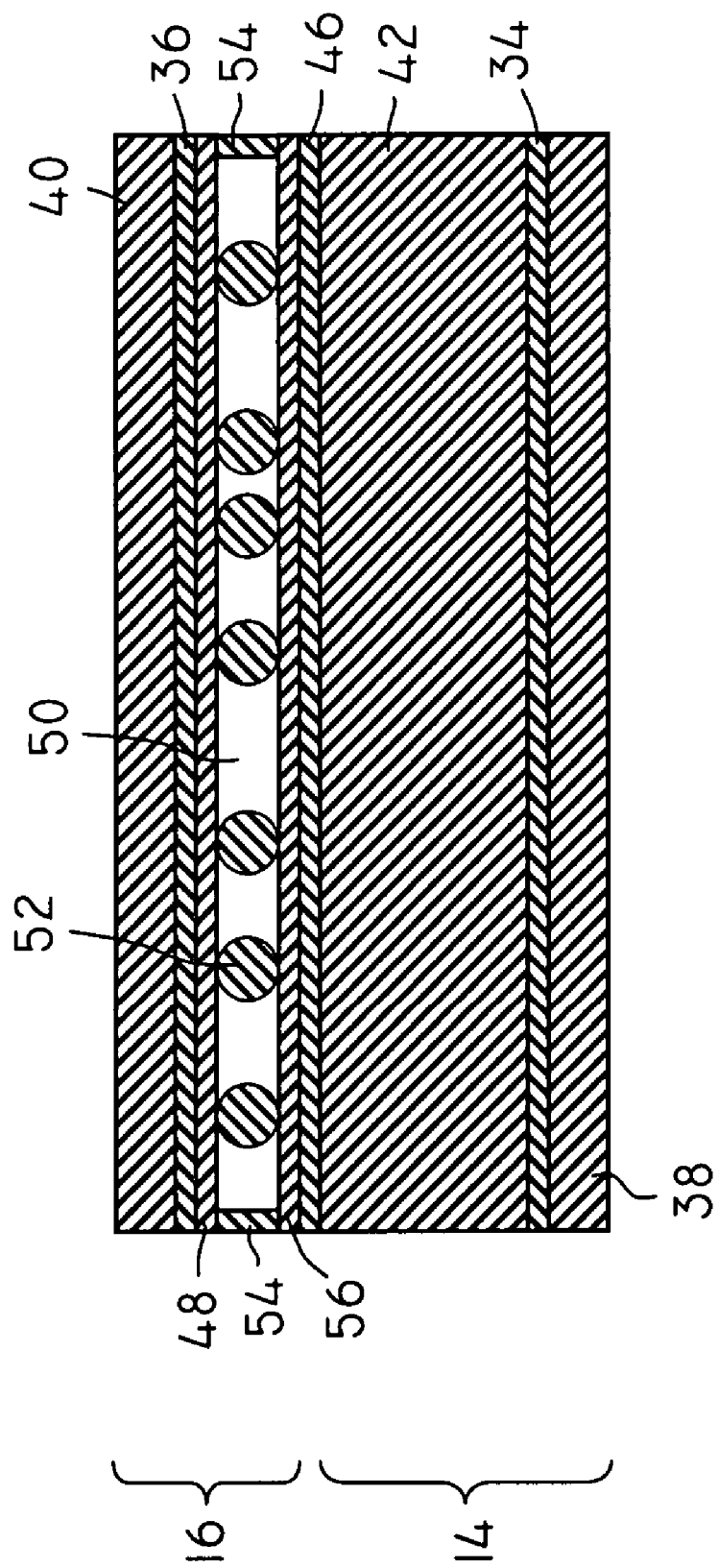
FIG. 2 is a cross-sectional view of an x-ray light valve, forming part of the digital radiographic imaging system of FIG. 1.

Turning now to FIG. 2, the XLV 12 is better illustrated. In the standard, preferred embodiment is composed of amorphous selenium as the photoconductor 14 combined with a liquid crystal cell used as the electro-optic modulator 16, and transparent electrodes, 34 and 36, on either side.

In the currently preferred construction method, two transparent substrates, 38 and 40, with deposited electrodes, 34 and 36, are used. One preferred substrate implementation is glass plates, with Indium Tin Oxide (ITO) electrodes, 34 and 36. The layer of amorphous selenium 42 is deposited onto one of them. When used in reflective configuration, the substrate on the photoconductor side 38 does not need to be transparent and a metal plate can be used instead, preferably aluminum, with the plate acting as an electrode and the metal oxide acting as a blocking layer. Although, using glass for both substrates 38 and 40 has the advantage that visible light can be provided from the side of the photoconductor 14. The layer of amorphous selenium 42 is deposited across the area of the substrate 38, with a thickness set to achieve a desired level of x-ray absorption efficiency, usually in a range from about 50 to about 5000 µm. If desired, an additional layer or layers 46 is deposited onto the amorphous selenium 42 layer. Very thin alignment layers, 48 and 56, are then applied on both surfaces. They are then cured and formed by using light, mechanical rubbing, or other means.

Both substrates 38 and 40, with all the additional layers 42, 46, 56, and 48, are subsequently made into a sandwich structure that will contain the liquid crystal 50. The transparent substrate 40 with the alignment layer 48 is placed in a spacer distributor and sprayed with spacers 52. The purpose of the spacers 52 is to keep a constant gap, which will later be filled with the liquid crystal 50. Adhesive 54 is placed around the perimeter of the transparent substrate 40 with the alignment layer 48, allowing an opening (neck) for the liquid crystal 50 to be added later. The two substrates, 38 and 40, with all the additional layers 42, 46, 56, and 48 in place, are then sandwiched together and placed in a press to ensure that the correct cell gap is maintained while the adhesive 54 cures. The cured structure is put in a vacuum chamber, which is evacuated. The liquid crystal 50 is then added at the location of the neck in the adhesive gasket using a vacuum manipulator and allowed to fill the cell by capillary action. Once the cell is filled, it is pressed again to ensure a correct gap, and sealed (while under pressure), producing the finished XLV 12.

The choice of liquid crystal 50 used in the cell varies the properties of the resulting electro-optic light modulator 16. By using high-resistivity liquid crystals designed for active-matrix liquid-crystal displays, the capability of keeping charge can be greatly increased. Such high-resistivity liquid crystals are designed for applications, where charges need to be stored in the pixel of a liquid-crystal display until the pixel is addressed in the next driving frame. The capability of keeping charge is called Voltage Holding Ratio (VHR). It usually depends on the chemical structure of the liquid crystal, the alignment layer, the handling of the liquid-crystal cell, and other factors (water content, impurities, glass, etc.). Increased concentration of organic or inorganic impurities will reduce the VHR. Large VHR can only be achieved with high resistivity liquid-crystal mixtures and extra pure materials. To minimize organic contaminations, rigorous cleaning of the substrates and alignment layers based on linear photo-polymerization are important. By using ultra-pure materials, alignment layers 48 and 56 based on linear photo-polymerization, and a high-resistivity liquid crystal 50 in combination with rigorous cleaning procedures, proper handling, and avoiding contaminations, the electro-optic light modulator 16 can be configured to retain the optical image for a long period of time, typically on the order of minutes.

This is a novel development in the field in contrast to U.S. Pat. Nos. 6,052,432 and 5,847,499, and CA patent 2,228,325, where the electro-optic light modulator is selected to allow image decay immediately after the exposure, typically fast enough eliminate the need of a mechanism to erase it. Furthermore, the suggested acquisition of multiple images during the decay to improve the image quality or the dynamic range has been proven to be impractical thus far. The fast decay of the optical images requires that the optical image is captured at once. This is usually done with a high-end camera, which greatly increases the cost of the overall system. In the present invention, by making the optical image in the electro-optic light modulator 16 to last long enough, typically on the order of minutes, the high-end camera can be replaced with a much less expensive scan technology. The scan technology allows the complexity of the camera to be exchanged for the inconvenience of a slightly longer acquisition time. Furthermore, scan technology is much easily scalable without sacrificing pixel density, pixel count, or the overall cost of the system.

The liquid-crystal cell used as the electro-optic light modulator 16 may be designed to accommodate specific wavelength(s), viewing and electro-optical properties. However, the greatest variations come from using different liquid-crystal-cell designs. Current preferred implementations include transmissive and reflective twisted nematic cells with various twist angles, including a zero twist angle.

Although the preferred construction method described the liquid-crystal cell used as the electro-optic light modulator 16 as having the same alignment on both sides, other implementations might include alignment layers, 48 and 56, made from the same or different materials, which might have different properties, meaning that pre-tilt and alignment can vary from side to side of the liquid-crystal cell.

Between the photoconductor layer 14 and electro-optic light modulator 16, other layers can be added. In FIG. 2, their position is indicated by reference numeral 46. These layers 46 are often added to make use of existing liquid-crystal technology, with the additional constraint of not damaging the photoconductor 14. These extra layers 46 can be added for the purposes of electrically insulating, or chemically protecting the layers from each other. The protective layers 46 could further act as an insulator. When used with liquid crystals, the layer 46 can be a polarizer, enabling particular amplification and erasing techniques. In order to enhance the reflectivity of the photoconductor layer 14, a layer of small mirrors or a continuous mirror layer may also be used.

Instead of uniform electrodes 34 and 36, segmented electrodes or a segmented perimeter electrode can be laid out to create non-uniform field(s). This can imbue particular imaging properties or correct for any distortion in the field created during construction. These electrodes can be created through laser etching.

As discussed above, a key feature of the XLV 12 is that it is designed such that the charge image is stable over a few minutes at the photoconductor-modulator interface. As a result of this long lifetime, it is necessary to eliminate, or erase, the remaining charge at the interface before a new exposure is made. To do this, the voltage applied to the electrodes 34 and 36 is turned off and the photoconductor 14 is flooded with light 60 to which the photoconductor 14 is sensitive from light source 62. The charges produced will neutralize the remaining image charge. The XLV 12 is then ready to acquire a new x-ray image. This differs from previous technology, particularly U.S. Pat. Nos. 6,052,432 and 5,847,499, and CA patent 2,228,325, where the image decays so quickly that no erasing is necessary.

The scanning device in accordance with the present invention is very scalable, from very small to very large, without sacrificing cost efficiency or image quality. This differs from previous technology, particularly U.S. Pat. Nos. 6,052,432 and 5,847,499, and CA patent 2,228,325, which require a rapid readout device like a camera and capture the image at once. When scaled up, such systems will have to implement more than one camera, which will increase the complexity and the overall cost significantly.

The scanning device 18 uses a row or rows of sensors 70 that sweep across the length or width of the electro-optic light modulator 16. In the reflective configuration, which is illustrated in FIG. 3A, the row of sensors 70 can be attached to a scan head 90, which might also include accompanying optics 72, polarizers, 92 and 94, and the readout light source 28 with which the electro-optic light modulator 16 is illuminated. Alternately, FIG. 3B shows the transmissive configuration, where the light source 28 and the polarizer 92 can also be placed on opposite side of the XLV 12.

In another embodiment, in order to feed light 74 coming from the light source 28 evenly to the scanning device 18, a mechanism to deliver the light may be used. The preferred implementation is in the form of a light pipe 110 as illustrated for a reflective configuration in FIG. 4A, which takes in the readout light 74 from the light source 28 on one side and emits it along one long axis shining a row of light through the electro-optic light modulator 16 onto the photoconductor 14 to be reflected into the scanning device 18. Similarly, as illustrated in FIG. 4B for transmissive use, a light pipe 110 can be placed on the opposite side of the scanning device 18 to shine through the photoconductor 14 and the electro-optic light modulator 16. As will be appreciated by those of skill, multiple light sources 28 placed along the scanning device 18 or a light illuminating a larger area can be used as well. Alternatively, the light pipe 110 might also be extended into a dedicated layer, which is transparent for the x-rays, so that the light is applied evenly onto the photoconductor across a given area. This can either be one piece or tiled.

In a preferred implementation of the present device, the scan head 90 may include a row of lenses 72 and sensors 70, and a light source 28, preferably red LEDs, coupled to a light pipe 110. The scanning device is operated on a reflective liquid-crystal cell used as the electro-optic light modulator 16 with a single polarizer 98. During the acquisition of the optical image, the scanning device 18 moves across the electro-optic light modulator 16 as indicated by the arrow. Light is injected into the light pipe 110 and emitted out along its length. The light transmits through the polarizer 98 and the electro-optic light modulator 16. The light reflected by the photoconductor is transmitted back through the electro-optic light modulator 16 and the polarizer 98. After passing through the optics 72, the modulated light reaches the sensors 70. Although only one polarizer 98 is shown, if desired, two polarizers, 92 and 94, can be used instead, placed in the path of the incoming and outgoing beams. Although the polarizer 98 is shown as a layer disposed on the electro-optic light modulator 16, it may be a part of the scan head 90.

FIG. 5 shows another embodiment of the scanning device 18. In this embodiment, a beam splitter 114 is used to separate incoming from outgoing light. Similar to the previous embodiment, the readout light source 28 is located on the same side as the scanning device 18. In this embodiment, the readout light 74 transmits through the beam splitter 114 and the electro-optic light modulator 16. The light reflected by the photoconductor 14 is transmitted back through the electro-optic light modulator 16. After passing the beam splitter 114 a second time, the modulated light 74 is sent to the optics 72 and the sensors 70. If a liquid-crystal cell is used as the electro-optic light modulator 16, a polarizer 116 can be placed in position between beam splitter 114 and the electro-optic light modulator 16 or two polarizers 118 and 120, may be placed as shown with polarizer 118 between beam splitter 114 and light source 28 and polarizer 120 is placed between beam splitter 114 and scanning device 18. As will be appreciated by those skilled in the art, a polarizing beam splitter may be used instead.

As will also be appreciated by those of skill in the art, some electro-optic light modulators 16 may change the amount of scattered light as a result of applied potential. Therefore, to accommodate these types of electro-optic light modulators, the sensor 70 and optics 72 may be placed off axis from the light source 28 so as to only capture light that scatters from the electro-optic modulator 16.

Turning now to FIGS. 6A and 6B, the design can be further enhanced by using multiple layers of either photoconductor 14 or electro-optic light modulators 16. By using two layers of the electro-static modulator 16 on either side of the photoconductor 14, as shown FIG. 6A, two parallel images from the same exposure can be created in reflective configuration. These images can also be formed with different types of electro-static light modulator 16, one on either side, allowing the images to compliment each other with different image properties. Similarly, as illustrated in FIG. 6B, a transmissive structure with a layer of photoconductor 14 on each side of the electro-optic modulator 16 would increase x-ray absorption efficiency.

Although the digital radiographic imaging system 10 has been described to include only of one XLV 12, some embodiments may include multiple XLVs with identical or different properties for the purpose of obtaining different types of data. For example, the digital x-ray imaging system 10 can use multiple XLVs designed to have a different x-ray response to acquire multiple images from the same exposure, which might then be synthesized into a digital image with greater dynamic range. Further, the XLVs might be designed to compliment each other by making use of different properties of different types of electro-optical light modulators or photoconductors.

Single or multiple wavelengths of light can be generated by the light sources 28 and 62. These wavelengths can be tuned either to react to different characteristics of the electro-optic modulator 16 or to interact with the photoconductor 14 in a particular way. For instance, the wavelength of the readout light 74 used during the acquisition of the static optical image is chosen either for quality of readout or to minimize image erasure. In contrast, during the reset phase of the XLV 12, the light 60 is deliberately tuned to erase the XLV 12. Further applications of the light sources 28 or 62 might include biasing of the photoconductor, partial erasing, or pre-conditioning of the XLV 12. Erasing procedures can involve light sources mounted on the scan head 90 and/or positioned stationary.

The parameters of electro-optic light modulator 16 are tuned as best as possible to a specific frequency or frequencies of the readout light 74 from light source 28. If desired, multiple frequencies of readout light 74 can be used. The preferred implementations include visible colours, IR, Ultraviolet or several different shades of one colour. Any combination of colours can be conducive to reading out the most information possible. For example, different wavelengths of readout light 74 experience different optical responses as a function of x-ray exposure when a liquid-crystal cell is used as the electro-optic light modulator 16.

In operation, the object 20 to be imaged is placed between the x-ray source 22 and the x-ray imaging system 10. An exposure bias potential is applied to the electrodes, 34 and 36. The exposure bias potential depends on the thickness of the XLV 12. The electric field required in the photoconductor layer 14 is usually in a range of about 5 to about 100 V per micron. For example, if the thickness of the photoconductor layer is 1000 microns and the thickness of the electro-optic light modulator is 5 microns, an exposure bias potential of 10,050 V will be applied to the electrodes 34 and 36 to achieve an electric field of 10 V per micron in the photoconductor 14. The x-ray source 22 is then operated to emit x-rays 26 which pass through the object 20. The photoconductor layer 14 in turn absorbs the x-rays 26 and creates charges, which are guided to the photoconductor-modulator interface (junction between layers 14 and 16) by the electric field created between the electrodes 34 and 36. The charges follow the electric field lines, ensuring that there is very little lateral spread as the charges move. The resulting charge image collected at the photoconductor-modulator interface faithfully reproduces the absorbed x-ray intensity pattern, causing spatial variations in the electric field across the electro-optic light modulator 16. Hence, a static optical image is formed, which is stored in the electro-optic light modulator 16. Once the object 20 has been exposed for a time sufficient to generate the desired static optical image, the x-ray source 22 is turned off and the exposure bias is removed. The optical image stored in the electro-optic light modulator 16 is subsequently digitized by using the light source 28 and the optical scanning device 18, sweeping across it as indicated by the arrow.

It is common for electro-optic light modulators to have a threshold voltage, which has to be reached before they can respond optically. The consequence is that some parts of the charge image created in the photoconductor will not be represented in the static optical image. In order to avoid this situation, there are several methods of biasing the XLV 12 during digitization of the optical image after a given x-ray exposure. These techniques aim to bring the electro-optic light modulator 16, particularly in case of a liquid-crystal cell, to the threshold of its operating characteristic, to enhance the signal, reduce the noise, or shift the optical response as a function of exposure. The XLV 12 can be biased using radiation. This can be done by using light source 62, performing a flood field exposure with light 60 to which the photoconductor is sensitive and creating additional uniformly distributed charge in the ptoconductor 14. Although in FIG. 1 light source 62 is indicated to be on the photoconductor 14 side of the XLV 12, in different embodiments it might be positioned to illuminate the photoconductor 14 through the electro-optic light modulator 16. Radiation based biasing can be performed before or after x-ray exposure. It can also be done during the digitization phase by using light source 28 with the readout light 74 tuned to a wavelength to which the photoconductor is sensitive.

Alternatively, the XLV 12 can be biased directly by applying a readout bias potential to the electrodes 34 and 36 during digitization of the optical image. The electric field required in the electro-optic light modulator 16 is usually in a range of about 0 to about 4 V per micron. For example, if the threshold voltage of the electro-optic light modulator is 1 V, the thickness of the photoconductor layer 14 is 1000 microns, and the thickness of the electro-optic light modulator 16 is 5 microns, the inventors need to apply to the electrodes 34 and 36 a readout bias potential of 201 V to overcome the threshold voltage. Higher readout bias potentials are used to increase the signal. Lower bias potentials are used to reduce the effect of offset signal. This is a novel development in the field in contrast to U.S. Pat. Nos. 6,052,432 and 5,847,499, and CA patent 2,228,325, which do not use a readout bias potential during the capture of the optical image. The previous technology relies on a bias light to emit actinic light onto the photoconductor prior formation of an x-ray exposure. Using a readout bias potential is a much more flexible and convenient way to shift the response characteristics of the electro-optic light modulator. It allows multiple shifts to be done on a single x-ray exposure, which is not possible when the biasing is done with actinic light.

Further, the voltage applied to the electrodes 34 and 36 can be modified during digitization by stepping it through predefined bias levels. The time of a step should be greater then the time needed to digitize one row. Multiple digitizations can be done in one position while the voltage is stepped and subsequently advancing the scan head 90 to the next position. Alternatively, a multiple or single head scanner may revisit a given position for multiple digitizations but at a different bias voltage. This would result in multiple digital images with a varied readout bias and hence slightly shifted characteristic curve. These digital images can be synthesized into a composite image with greater dynamic range then one image alone. Also, multiple digitizations at the same bias voltage or without a bias voltage applied might also be useful for further image processing.

Some electro-optical light modulators 16, particularly liquid-crystal cells, may be designed to have multi-valued response as a function of x-ray exposure, where a signal value can correspond to several different x-ray exposures. The particular exposure can be determined by either modifying the potential applied to the electrodes 34 and 36 during the digitization of the optical image or using multiple wavelengths of the readout light 74. In particular, an image can be synthesized by using the above ramping bias voltage method.

There are multiple methods that can be used for the erasure of XLV 12, and some can be used for specific circumstances. The preferred implementation consists of shining unfiltered white light 60 onto the photoconductor 14 while the electrodes 34 and 36 are shorted. Different implementations might place the electrodes in open circuit, closed circuit, grounded or at a specific voltage, before, after or during the shining of light 60. The light source 28 or multiple sources of light can placed on the side of the photoconductor 14 or/and on the side of the electro-optic light modulator 16. These methods, although known as erasing methods, can at times also be used to enhance the image acquisition process.

Further, there are methods whereby the XLV 12 is shunted through a series of states to combine both erasing and pre-conditioning of the XLV 12 into one procedure. One such method is to reverse the voltage on the electrodes 34 and 36 of the XLV 12 from its operating voltage, shine light 60 to erase and pre-charge the XLV 12, and then reverse the voltage applied to the electrodes 34 and 36 to normal. This should result in an erased image and higher voltages on the photoconductor 14 and lower voltages on the electro-optic modulator 16.

Another obstacle that can be encountered in acquiring images is the presence of ions in the electro-optic light modulator 16. A possible solution is to generate uniformly distributed charge created with light 60 to which the photoconductor 14 is sensitive before the x-ray exposure. The created charge should be sufficient to attract the free ions in the electro-optic light modulator and neutralize them at the surface, eliminating the ions from further interaction with charge of the charge image created later by the x-ray exposure.

Potential can also be applied in such a manner as to reduce the dark current in the XLV 12. This is accomplished by applying a potential to the electrodes 34 and 36 and creating a conditioning field, which is larger than the field before the x-ray exposure. Once the conditioning is finished, the field is dropped to the lower field, and the exposure and readout are carried out normally.

The individual sensors in the scanning device 18 may need to be calibrated. The calibration uses uniform areas of the electro-optical light modulator 16 or specially-designed patches with specific reflective, transmissive, or scattering properties to acquire data, which is used to correct for illumination, gain, offset differences of the individual sensor elements 70. The preferred implementation advances the scan head 90 to a non-reflective patch to adjust for differences in the dark signal (offset) and to a reflective patch, like a mirror, to adjust the signal level corresponding to a maximum reflection (gain). Different implementations might include an area of the liquid-crystal cell which does not contain any liquid crystal.

In a preferred implementation, the operation of the radiographic digital x-ray imaging system 10 based on a XLV 12 and scanning device 18 operated in reflective configuration follows these steps:

1. The scan system 18 is calibrated across its sensors.

2. A reference digitization of the electro-optic light modulator 16 is acquired to ensure that the previous optical images are erased.

3. The exposure bias potential is applied to the electrodes 34 and 36 to create a field in the photoconductor 14.

4. An exposure of x-rays 26 is made, which are absorbed in the photoconductor 14 after penetrating the object 20.

5. The exposure bias is removed and a readout bias potential may be applied to the electrodes 34 and 36.

6. The absorbed x-rays create a static optical image, which is now stored in the electro-optic light modulator 16.

7. The stored optical image is subsequently digitized by using a readout light source 28 and moving an optical scanning device 18 across it.

8. The readout bias potential is removed and the electrodes 34 and 36 are shorted.

9. The XLV 12 is erased by using light source 62.

10. The digital image is processed and stored by a processor 30.

The inventors have further discovered that, under low x-ray exposures, by using high-resolution optics 72 to observe the electro-optic light modulator 16 as part of the scanning device 18, the charge clouds of the individual x-rays 26 are visible and can be counted. If the x-ray imaging system 10 counts individual x-rays 26, then the gray scale levels in the final composite digital image can be the actual photon counts per unit area instead of optical signal which is proportional to the number of x-rays. This will completely eliminate electronic noise at low x-ray exposures. This digital image can further be manipulated into emulating film or any other type of detector.

Although the XLV 12 has been described as including an electro-optic light modulator 16 in the form of a twisted nematic liquid-crystal cell, it should be appreciated that other types of liquid-crystal cells or other suitable electro-optic light modulators like cells based on electrowetting or electrophoretic ink might be used.

Also, although the photoconductive detector layer has been described as including amorphous selenium, those of skill in the art will appreciate that other photoconductive materials like CdZnTe, Si, or Ge may also be used.

Although the digitization of the optical image has been described to be done by a scanning device, other devices, such as for example cameras or light sensitive matrices can be used as well. Furthermore, the optics may be replaced with another type of optical coupler such as fiber optics.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

REFERENCES CITED

U.S. Patent Documents

U.S. Pat. No. 5,847,499:
"Apparatus for generating multiple X-ray images of an object from a single X-ray exposure"
Rieppo; Pia Krista M.; Rowlands; John A.
U.S. Pat. No. 6,052,432:
"Method of generating multiple x-ray images of an object from a single x-ray exposure"
Rieppo; Pia Krista M.; Rowlands; John A.
U.S. Pat. No. 4,368,386
"Liquid-crystal image converter device"
Huignard; Jean-Pierre, Le Berre; Serge, Mayeux; Christian; Micheron; Francois Canadian Patent Documents CA Patent 2,228,325
"X-ray image intensifier"
Rieppo; Pia Krista M.; Rowlands; John A

OTHER REFERENCES

1. P. K. Rieppo, B. Bahadur, and J. A. Rowlands, "Amorphous selenium liquid crystal light valve for x-ray imaging", in R. L. Van Metter and J. Beutel, Eds., *Physics of Medical Imaging*, Proc. SPIE 2432, 228-236.
2. P. K. Rieppo and J. A. Rowlands, "X-ray imaging using amorphous selenium: Theoretical feasibility of the liquid crystal light valve for radiography", *Medical Physics*, 24, 1279-1292 (1997). 10.
3. P. Rieppo, "An Amorphous Selenium X-Ray Light Valve for Diagnostic Radiography," M. Sc. Thesis, University of Toronto, 1996.
4. Mark J. Foley, Philip W. Walton, Wil van der Putten, Adam Workman, "Small Area CCD Based Imaging System for use in Digital Mammography," proceedings of the 7$^{th}$ IWDM 2004
5. Mark J. Foley, Philip W. Walton, and Wil van der Putten, "Development of an image receptor for use in Digital Mammography," proceedings of SPIE Vol. 4876, 54-60 (2003).

Therefore what is claimed is:

1. A digital radiographic imaging system, comprising:
  a) an x-ray light valve including a first photoconductive detector layer and an electro-optic light modulator disposed on said first photoconductive detector layer, said electro-optic light modulator being configured to store optical images induced therein for a pre-selected period of time, means for applying and removing an exposure bias potential across said x-ray light valve such that when said exposure bias potential is applied an electric field is produced in said x-ray light valve and hence across said first photoconductive detector layer,
  whereupon exposing said x-ray light valve to x-rays having passed through an object to be imaged to form an x-ray exposure of said object, said first photoconductive detector layer absorbing x-rays having passed through said object forming electron-hole pairs separated by said exposure bias potential thereby to form a charge image which corresponds to the absorbed x-rays creating variations in potential across said electro-optic modulator, and upon removing said exposure bias potential the charge image induces an entire static optical image of said x-ray exposure in the electro-optic light modulator, which is stored in the electro-optic light modulator and lasts for said pre-selected period of time without changes to said entire static optical image to enable capture of said entire static optical image by scanning;
  b) a readout light source configured to illuminate a portion of said entire static optical image stored in said electro-optic light modulator, said variations in potential across said electro-optic modulator modulating an intensity of said readout light illuminating said portion of said entire static optical image thereby to create an optical representation of said x-ray exposure;
  c) an optical imaging device positioned at a pre-selected position with respect to said x-ray light valve to receive said modulated intensity of readout light capturing said portion of said stored entire static optical image of said x-ray exposure;
  d) a scanning mechanism to which said optical imaging device is attached which is configured for moving said optical imaging device with respect to said x-ray light valve to enable sequential capture of some or all portions of said entire static optical image over said pre-selected period of time; and
  e) a processor coupled to said optical imaging device to digitize, produce and store a digitized version of some or all portions of said entire static optical image of said x-ray exposure.

2. The system according to claim 1 including an x-ray source mounted with respect to said x-ray light valve to generate x-rays to pass through said object to be imaged.

3. The system according to claim 1 including means for applying a readout bias potential to said x-ray light valve which is sufficient to overcome a threshold voltage of the electro-optic light modulator.

4. The system according to claim 1 wherein said optical imaging device includes at least one single sensor element.

5. The system according to claim 1 wherein said optical imaging device includes multiple sensor elements arranged in a row.

6. The system according to claim 1 wherein said optical imaging device includes multiple sensor elements arranged in multiple rows.

7. The system according to claim 1 wherein said optical imaging device includes multiple sensors arranged in multiple rows, and wherein said readout light source includes multiple readout light sources, and wherein each of said multiple readout light sources is paired with at least one of said multiple rows of said sensor elements.

8. The system according to claim 7 wherein each of said multiple readout light sources has a pre-selected spectral output and wherein said sensor element associated with a particular readout light source is tuned to said pre-selected spectral output of that readout light source.

9. The system according to claim 1 wherein said readout light source emits single or multiple wavelengths in infrared, visible, or ultraviolet spectra selected to not eliminate charges creating variations in potential across said electro-optic modulator thereby to form an entire static optical image stored in said electro-optic light modulator.

10. The system according to claim 1 wherein said readout light source is configured to emit at one or more wavelengths selected to create additional uniformly distributed charge in said first photoconductive detector layer sufficient to overcome a threshold voltage of the electro-optic light modulator.

11. The system according to claim 1 wherein said readout light source emits single or multiple wavelengths in infrared, visible, or ultraviolet spectra selected to use different electro-optic characteristics of said electro-optic light modulator, whereby electro-optic characteristics of said electro-optic modulator depends on the wavelength of said readout light used.

12. The system according to claim 1 including a light pipe, wherein said readout light source is optically coupled to said light pipe evenly to illuminate said portion of said entire static optical image stored in said electro-optic light modulator.

13. The system according to claim 1 including a light source emitting light with wavelengths selected to erase said entire static optical image of said x-ray exposure.

14. The system according to claim 13 wherein said light source emits white light.

15. The system according to claim 1 wherein said first photoconductive detector layer is made of amorphous selenium and said electro-optic light modulator is a liquid crystal cell containing liquid crystal.

16. The system according claim 15 wherein said liquid crystal cell is one of a transmissive or a reflective twisted-nematic liquid-crystal cell with a constant twist angle selected from a variety of possible twist angles, including a zero twist angle.

17. The system according to claim 1 including a beam splitter located on the same side of the x-ray light valve as said read out light source between said x-ray light valve and said optical imaging device, whereby said beam splitter is used to direct light from said readout light source into said x-ray light valve to illuminate said portion of said entire static optical image stored in said electro-optic light modulator and to separate said readout light modulated by electro-optic light modulator from said readout light, wherein said readout light modulated by electro-optic light modulator is transmitted by said beam splitter to said optical imaging device.

18. The system according to claim 17 wherein said beam splitter is a polarizing beam splitter.

19. The system according to claim 17 including a polarizer located between said beam splitter and said electro-optic light modulator.

20. The system according to claim 17 including a first polarizer located between said beam splitter and said readout light source and a second polarizer located between said beam splitter and said optical imaging device.

21. The system according to claim 1 including an additional layer disposed between said first photoconductive detector layer and said electro-optic light modulator, whereby said additional layer functions as any one of a protective layer, insulating layer, polarizing layer, reflective layer, and any combination thereof.

22. The system according to claim 1 wherein said means for applying and removing said exposure bias potential across said x-ray light valve includes one of segmented electrodes and a segmented perimeter electrode, wherein said segmented electrodes or said segmented perimeter electrode are used to apply non-uniform bias potential to x-ray light valve such that a non-uniform electric field is produced in said x-ray light valve and hence across said first photoconductive detector layer.

23. The system according to claim 3 wherein said means for applying and removing said readout bias potential across said x-ray light valve includes one of segmented electrodes and a segmented perimeter electrode, wherein said segmented electrodes or said segmented perimeter electrode are used to apply non-uniform bias potential to x-ray light valve such that a non-uniform electric field is produced in said x-ray light valve and hence across said electro-optic light modulator.

24. The system according to claim 1 including one or more pre-selected positions with any one of specific reflective, transmissive, scattering properties and any combination thereof, said pre-selected positions are used to calibrate said optical imaging device including adjusting readout light intensity and gain and offset of said at least one single sensor element.

25. The system according to claim 18 wherein said readout light source is geometrically positioned with respect to said optical imaging device such that the optical imaging device, said portion of said entire static optical image and said readout light source have a transmissive configuration aligned along a common axis with said optical imaging device on one side of said x-ray light valve and said readout light source located on the other side so that the light is transmitted through said first photoconductive detector layer and said electro-optic light modulator.

26. The system according to claim 25 wherein said readout light source is attached to said scanning mechanism and moved in tandem with said optical imaging device.

27. The system according to claim 1 wherein said readout light source is geometrically positioned with respect to said optical imaging device in a reflective configuration such that said optical imaging device and said readout light source are located on the same side of the x-ray light valve so that light detected by the optical imaging device is directly reflected off said first photoconductive detector layer.

28. The system according to claim 27 wherein said readout light source is attached to said scanning mechanism and moved in tandem with said optical imaging device.

29. The system of claim 1 wherein said readout light source is geometrically positioned with respect to said optical imaging device such that said optical imaging device and said readout light source have an off-axis configuration so that light scattered off said electro-optic light modulator is detected by said optical imaging device.

30. The system according to claim 29 wherein said readout light source is attached to said scanning mechanism and moved in tandem with said optical imaging device.

31. The system of claim 1 including a second electro-optical light modulator, a second readout light source, and a second optical imaging device, wherein the two electro-optic light modulators are placed on either side of said first photoconductive detector layer and wherein each said optical imaging device is paired with an associated readout light source in a reflective configuration such that said optical imaging device and associated readout light source are located on the same side of the x-ray light valve so that modulated readout light captured by the optical imaging device is directly reflected off said first photoconductive detector layer.

32. The system according to claim 31 wherein each readout light source is attached to said scanning mechanism and moved in tandem with said associated optical imaging device.

33. The system of claim 1 including a second photoconductive detector layer, wherein the first and second photoconductive detector layers are placed on either side of said electro-optic light modulator and wherein said readout light source is geometrically positioned with respect to said optical imaging device such that said optical imaging device, said portion of said entire static optical image and said readout light source have a transmissive configuration aligned along a common axis with said optical imaging device located on one side of said x-ray light valve and said readout light source located on the other side so that said readout light is transmitted through, said first photoconductive detector layer, said electro-optic light modulator and said second photoconductive detector layer.

34. The system according to claim 33 wherein said readout light source is attached to said scanning mechanism and moved in tandem with said optical imaging device.

35. The system of claim 1 including focusing optics positioned between said x-ray light valve and said optical imaging device for directing and focusing light from said portion of said entire static optical image on said optical imaging device.

36. The system of claim 35 wherein said focusing optics and said sensor elements are configured to give sufficient resolution to distinguish charge clouds of individual x-ray photons absorbed in said photoconductor and contributing to said charge image inducing an entire static optical image of said x-ray exposure in the electro-optic light modulator.

37. The system according to claim 15 wherein said liquid crystal in said liquid-crystal cell is a high-resistivity liquid crystal.

38. The system according to claim 1 including a polarizer located between said electro-optic light modulator and both said optical imaging device and said readout light source.

39. The system according to claim 1 including a first polarizer located between said readout light source and said electro-optic light modulator and a second polarizer located between said electro-optic light modulator and said optical imaging device.

40. The system of claim 1 wherein said readout light source includes focusing optics for directing and focusing light from said readout light source to said x-ray light valve.

41. The system of claim 37 wherein said liquid crystal cell includes opposed alignment layers and with spacers therebetween to keep a gap between said alignment layers, said gap being filled with liquid crystal, said alignment layers and being produced using linear photo-polymerization.

42. The system of claim 41 wherein said high-resistivity liquid crystal cell is produced under conditions suitable to reduce contamination by organic and inorganic impurities.

43. A method of x-ray imaging of an object, comprising the steps of:
   a) applying an exposure bias potential across a x-ray light valve which includes a photoconductive detector layer and an electro-optic light modulator disposed on said photoconductive detector layer such that an electric field is produced in said x-ray light valve and hence across said photoconductive detector layer;
   b) exposing said x-ray light valve to x-rays having passed through an object to be imaged to form an x-ray exposure of said object, said photoconductive detector layer absorbing x-rays having passed through said object forming electron-hole pairs separated by said exposure bias potential thereby to form a charge image which faithfully corresponds to the absorbed x-rays creating variations in potential across said electro-optic modulator;
   c) removing said exposure bias potential whereupon the charge image induces an entire static optical image of said x-ray exposure in the electro-optic light modulator, said electro-optic light modulator being configured such that said electro-optic light modulator retains said entire static optical image for a pre-selected period of time without changes to said entire static optical image to enable capture of said entire static optical image to continue over said pre-selected period of time by scanning;
   d) illuminating a portion of said entire static optical image of said x-ray exposure stored in said electro-optic light modulator
   e) capturing said portion of the entire static optical image of said x-ray exposure using an optical imaging device;
   f) digitizing and storing said captured portion of said entire static optical image of said x-ray exposure;
   g) moving said optical imaging device with respect to said x-ray light valve using a scanning mechanism and repeating steps d), e) and f) to sequentially capture all portions of said entire static optical image within said pre-selected period of time.

44. The method according to claim 43 wherein said electric field is produced in said x-ray light valve and hence across said photoconductive detector layer is in a range from about 5 to about 100 volts per micron.

45. The method according to claim 43 including a step of applying a readout bias potential to said x-ray light valve such that an electric field is produced in said x-ray light valve and hence across said electro-optic light modulator after step c) and prior to step d) which is sufficient to overcome a threshold voltage of said electro-optic light modulator, and maintaining said readout bias potential for steps d) e), f) and g).

46. The method according to claim 45 wherein said electric field is produced in said x-ray light valve and hence across said electro-optic light modulator is in a range from about 0 to about 4 volts per micron.

47. The method according to claim 43 including after step g) combining at least some of said digitized and stored portions to produce a digitized version of said part of said entire static optical image of said x-ray exposure.

48. The method according to claim 43 including after step g) combining all digitized and stored portions of said entire static optical image of said x-ray exposure to produce a digitized version of said entire static optical image of said x-ray exposure.

49. The method according to claim 43 wherein after step g), including a step of illuminating said x-ray light valve with light to erase said entire static optical image of said x-ray exposure.

50. The method according to claim 45 wherein after step g), including changing said readout bias potential to a different readout bias potential and repeating steps d) to g) at said different readout bias potential.

51. The method according to claim 50 wherein after step f), including step
h) of changing said readout bias potential to a different readout bias potential and repeating steps d), e) and f) at said different readout bias potential,
step i) repeating step h) for a pre-selected number of different readout bias potentials, thereafter
performing step g) and performing steps h) and i) during each of steps e), f) and g).

52. The method according to claim 43 wherein said step d) of illuminating a portion of said entire static optical image of said x-ray exposure stored in said electro-optic light modulator includes using a readout light source geometrically positioned with respect to said optical imaging device such that said optical imaging device, said portion of said entire static optical image and said readout light source have a transmissive configuration aligned along a common axis with said optical imaging device on one side of said x-ray light valve and said readout light source is located on the other side so that said readout light is transmitted through said photoconductive detector layer and said electro-optic light modulator.

53. The method according to claim 52 wherein said readout light source is moved in tandem with said optical imaging device.

54. The method according to claim 43 wherein said step d) of illuminating a portion of said entire static optical image of said x-ray exposure stored in said electro-optic light modulator includes using a readout light source geometrically positioned with respect to said optical imaging device in a reflective configuration such that said optical imaging device and said readout light source are located on the same side of said x-ray light valve so that said readout light detected by said the optical imaging device is directly reflected off said photoconductive detector layer.

55. The method according to claim 54 wherein said readout light source is moved in tandem with said optical imaging device.

56. The method according to claim 43 wherein said step d) of illuminating a portion of said entire static optical image of said x-ray exposure stored in said electro-optic light modulator includes using a readout light source geometrically positioned with respect to said optical imaging device such that said optical imaging device and said readout light source have an off-axis configuration so that light detected by said optical imaging device is scattered off said electro-optic light modulator.

57. The method according to claim 56 wherein said readout light source is moved in tandem with said optical imaging device.

58. The method according to claim 43 wherein prior to step a), including a step of moving said optical imaging device to a pre-selected position with specific reflective, transmissive, or scattering properties to calibrate said optical imaging device.

59. The method according to claim 58 wherein the pre-selected position is part of said x-ray light valve.

60. The method according to claim 43 wherein said step of applying an exposure bias potential includes using one of grid of electrodes and a segmented perimeter electrode to apply a non-uniform bias potential to x-ray light valve such that a non-uniform electric field is produced in said x-ray light valve and hence across said photoconductive detector layer.

61. The method according to claim 45 wherein said step of applying an readout bias potential includes using a grid of electrodes or a segmented perimeter electrode to apply a non-uniform bias potential to x-ray light valve such that a non-uniform electric field is produced in said x-ray light valve and hence across said electro-optic light modulator.

62. The method according to claim 43 including before step a) or after step c) and before step d) a step of applying a bias potential to said x-ray light valve and illuminating said x-ray light valve with light selected to create uniformly distributed charge in said photoconductive detector layer which is sufficient to overcome a threshold voltage of said electro-optic light modulator.

63. The method according to claim 43 wherein before step a) including a step of applying a bias potential to said x-ray light valve and illuminating said x-ray light valve with light selected to create uniformly distributed charge sufficient to attract and neutralize free ions in said electro-optic light modulator and eliminating them from further interaction with said charge image created by said x-ray exposure.

64. The method according to claim 45 wherein said step d) of illuminating a portion of said entire static optical image of said x-ray exposure stored in said electro-optic light modulator includes using a readout light source selected to create charge in said photoconductive detector layer which is sufficient to overcome a threshold voltage of the electro-optic light modulator.

65. The method according to claim 43 including after step g) a step of counting the number of the individual x-ray photons per unit area in said static optical image to be used as a gray level representation of said x-ray exposure.

66. The method according to claim 49 including applying a bias potential or a sequence of potential reversals.

67. The method according to claim 43 wherein prior to obtaining another x-ray image, including a step of applying a sequence of potential reversals to said x-ray light valve to erase said entire static optical image of said x-ray exposure.

68. The method according to claim 43 wherein prior to obtaining another x-ray image steps d), e), f), and g) are repeated to ensure that the previous optical image is erased.

69. The method according to claim 43 including a step of applying a readout bias potential to said x-ray light valve after step c) and prior to step d) which is sufficient to overcome the ambiguity of a multi-valued electro-optic light modulator, and maintaining said readout bias potential for steps d), e), f) and g).

70. The method according to claim 43 wherein after step g), including changing of wavelength of said readout light to a different wavelength and repeating steps d) to g) with said different wavelength of said readout light.

71. The method according to claim 43 wherein after step f), including step j) of changing the wavelength of said readout light to a different wavelength and repeating step d), e), and f) with said different wavelength,
step k) repeating step j) for a pre-selected number of different said wavelengths, thereafter
performing step g) and performing step j) and k) during each of steps d), e) and f).

* * * * *

UNITED STATES PATENT AND TRADEMARK OFFICE
CERTIFICATE OF CORRECTION

PATENT NO. : 7,687,792 B2 Page 1 of 1
APPLICATION NO. : 11/704371
DATED : March 30, 2010
INVENTOR(S) : Rowlands et al.

It is certified that error appears in the above-identified patent and that said Letters Patent is hereby corrected as shown below:

Please amend claim 25 of the issue patent as follows:
25. The system according to claim [[18]] 1 wherein said readout light source is geometrically positioned with respect to said optical imaging device such that the optical imaging device, said portion of said entire static optical image and said readout light source have a transmissive configuration aligned along a common axis with said optical imaging device on one side of said x-ray light valve and said readout light source located on the other side so that the light is transmitted through said first photoconductive detector layer and said electro-optic light modulator.

Signed and Sealed this

Sixteenth Day of November, 2010

David J. Kappos
*Director of the United States Patent and Trademark Office*

UNITED STATES PATENT AND TRADEMARK OFFICE
CERTIFICATE OF CORRECTION

PATENT NO. : 7,687,792 B2  Page 1 of 1
APPLICATION NO. : 11/704371
DATED : March 30, 2010
INVENTOR(S) : Rowlands et al.

It is certified that error appears in the above-identified patent and that said Letters Patent is hereby corrected as shown below:

Column 16, lines 39-48, please amend claim 25 of the issue patent as follows:
25. The system according to claim [[18]] 1 wherein said readout light source is geometrically positioned with respect to said optical imaging device such that the optical imaging device, said portion of said entire static optical image and said readout light source have a transmissive configuration aligned along a common axis with said optical imaging device on one side of said x-ray light valve and said readout light source located on the other side so that the light is transmitted through said first photoconductive detector layer and said electro-optic light modulator.

This certificate supersedes the Certificate of Correction issued November 16, 2010.

Signed and Sealed this

Fourteenth Day of December, 2010

David J. Kappos
*Director of the United States Patent and Trademark Office*